US011908549B2

(12) United States Patent
Akse et al.

(10) Patent No.: US 11,908,549 B2
(45) Date of Patent: Feb. 20, 2024

(54) BAYESIAN INFERENCE

(71) Applicant: KONINKLIJKE PHILIPS N.V., Eindhoven (NL)

(72) Inventors: Martijn Theodorus Lambert Akse, Eindhoven (NL); Wilhelmus Franciscus Johannes Verhaegh, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 997 days.

(21) Appl. No.: 16/646,187

(22) PCT Filed: Sep. 21, 2018

(86) PCT No.: PCT/EP2018/075703
§ 371 (c)(1),
(2) Date: Mar. 11, 2020

(87) PCT Pub. No.: WO2019/063448
PCT Pub. Date: Apr. 4, 2019

(65) Prior Publication Data
US 2020/0273536 A1    Aug. 27, 2020

(30) Foreign Application Priority Data
Sep. 28, 2017  (EP) .................... 17193640

(51) Int. Cl.
*G16B 5/20*       (2019.01)
*G16B 40/00*      (2019.01)
(52) U.S. Cl.
CPC ............... *G16B 5/20* (2019.02); *G16B 40/00* (2019.02)
(58) Field of Classification Search
CPC .......... G16B 5/20; G16B 40/00; G16B 40/20
See application file for complete search history.

(56) References Cited

U.S. PATENT DOCUMENTS

2014/0156200 A1    6/2014  Alves et al.
2016/0117443 A1*   4/2016  Van Ooijen .......... C12Q 1/6886
                                                      514/249
(Continued)

FOREIGN PATENT DOCUMENTS

JP    2012212274 A    11/2012

OTHER PUBLICATIONS

Verhaegh, W. et al., "Selection of personalized patient therapy through the use of knowledge-based computational models that identify tumor-driving signal transduction pathways", Cancer Research, vol. 74, No. 11, 2014, pp. 2936-2945.

(Continued)

*Primary Examiner* — Robert J Eom

(57) ABSTRACT

The invention relates to a computer-implemented Bayesian inference method for performing Bayesian inference in a Bayesian network, which includes a continuous child node (3) and its discrete parent node (2) having two states. Being provided with a calibrated continuous probability distribution of the observations of the child node (3) for each of the two states of the parent node (2), the inferring for a new observation of the child node (3) for which the state of the parent node (2) is not known of the probability of at least a first state of the parent node (2) makes use of masses of portions of the probability distributions that depend on a locational relationship of the probability distributions and the value of the new observation. This may ensure that the inferred probability of the first state of the parent node (2) monotonically changes with monotonically changing values of the new observation.

20 Claims, 9 Drawing Sheets

(56) References Cited

U.S. PATENT DOCUMENTS

2016/0298196 A1 10/2016 Van De Stolpe et al.
2017/0046477 A1 2/2017 Van Ooijen
2018/0271438 A1 9/2018 Van De Stolpe et al.

OTHER PUBLICATIONS

Geyer, F.C. et al., "β-Catenin pathway activation in breast cancer is associated with triple-negative phenotype but not with CTNNB1 mutation", Modern Pathology, vol. 24, 2011, pp. 209-231.

Nodelman, U. et al., "Continuous Time Bayesian Networks". Artificial Intelligence. Appears in Proceedings of the Eighteenth Conference on Uncertainty in Artificial Intelligence. arXiv:1301.0591. (2002).

Yuan, C. et al., "How Heavy Should the Tails Be?" American Association for Artificial Intelligence. Conference Paper Jan. 2005.

Engelman, J.A., "Targeting P13K signaling in cancer: opportunities, challenges and limitations", Nature Reviews Cancer, No. 9, Aug. 2009, pp. 550-562.

Sempere, M.C. et al., "The role of the NFkB signaling pathway in cancer", Clinical and Translational Oncology, vol. 10, No. 3, Mar. 2008, Abstract.

Xia, L. et al., "Role of the NFkB-signaling pathway in cancer", Onco Targets and Therapy, vol. 11, Apr. 2018, pp. 2063-2073.

Colak, S. et al., "Targeting TGF-β signaling in cancer", Trends in Cancer, vol. 3, No. 1, Jan. 2017, pp. 56-71.

Thomas, S.J. et al., "The role of JAK/STAT signaling in the pathogenesis, prognosis and treatment of solid tumours", British Journal of Cancer, vol. 113, No. 3, Jul. 2015, pp. 365-371.

Duchartre, Y. et al., "The Wnt signaling pathway in cancer", Critical Reviews in Oncology/Hematology, vol. 99, Mar. 2016, pp. 141-149.

Acar, A. et al., "A role for Notch signaling in breast cancer and endocrine resistance", Stem Cells International, vol. 2016.

Renoir, J.M. et al., "Estrogen receptor signaling as a target for novel breast cancer therapeutics", Biochemical Pharmacology, vol. 85, No. 4, Feb. 2013, pp. 449-465.

Gupta, S. et al., "Targeting the Hedgehog pathway in cancer", Therapeutic Advances in Medical Oncology, vol. 2, No. 4, Jul. 2010, pp. 237-250.

Espinoza, I. et al., "Notch inhibitors for cancer treatment", Pharmacology & Therapeutics, vol. 139, No. 2, Aug. 2013, pp. 95-110.

International Search Report—PCT/EP2018/075703 dated Sep. 21, 2018.

* cited by examiner

BAYESIAN INFERENCE

CROSS-REFERENCE TO PRIOR APPLICATIONS

This application is the U.S. National Phase application under 35 U.S.C. § 371 of International Application No. PCT/EP2018/075703, filed on Sep. 21, 2018, which claims the benefit of EP Patent Application No. 17193640.4, filed on Sep. 28, 2017. These applications are hereby incorporated by reference herein.

FIELD OF THE INVENTION

The invention generally relates to technical fields where Bayesian networks and Bayesian inference are used, for example, bioinformatics, medicine, clinical decision support (CDS) systems and engineering. More particularly, the invention relates to a computer-implemented Bayesian inference method, device and computer program for performing Bayesian inference in a Bayesian network, which includes a continuous child node and its discrete parent node having two states. The invention further relates to a method for inferring activity of a cellular signaling pathway using probabilistic modelling of target gene expressions, in which the computer-implemented Bayesian inference method is applied.

BACKGROUND OF THE INVENTION

To allow for inference in a Bayesian network, i.e. updating probabilities for all nodes in the network given new evidence, the state space must be explicitly defined for all nodes in the Bayesian network and relationships between nodes need to be quantified in probabilistic terms by the use of conditional probability tables (CPTs). If the model has a known structure, these CPTs can be calibrated using complete data where the input and outcome of interest is known.

The standard approach in Bayesian networks discretizes the state space of nodes into a finite number of possible states and the CPTs are calibrated using complete datasets where the input and outcome of interest is known. However, if input data for a particular node is measured on a continuous scale, information is lost in the discretization process. The current solution to circumvent this loss of information is making use of continuous representations of nodes. Instead of discretizing the continuous calibration data, this data is used to estimate parameters of a continuous distribution, for example the mean and standard deviation of a normal distribution.

If the states of the nodes and the CPTs have been defined, Bayesian inference is used to obtain updated probabilities for all other states in the network if new evidence becomes available. For instance, consider the case where evidence is observed for a node where the calibration data distinguishes between two groups and from this data the normal distributions for group A and group B are estimated. Then, if new evidence is observed, one would like to know whether the obtained evidence is more likely to come from group A or from group B. The current solution, as available in e.g. the Bayes Net Toolbox for Matlab, finds the probability density at the evidence values for both groups and normalizes these values to obtain updated probabilities. This, however, does not ensure a monotonous relation between a continuous observation of a child node and the inferred state of its parent node.

SUMMARY OF THE INVENTION

It is therefore an object of the present invention to provide a computer-implemented Bayesian inference method, device and computer program which allow obtaining monotonically changing output probabilities with monotonically changing input values. It is a further object of the present invention to provide a method for inferring activity of a cellular signaling pathway using probabilistic modelling of target gene expressions, in which the computer-implemented Bayesian inference method is applied.

In a first aspect of the present invention a computer-implemented Bayesian inference method for performing Bayesian inference in a Bayesian network, which includes a continuous child node and its discrete parent node having two states, is presented, wherein the computer-implemented Bayesian inference method comprises:
a) providing a continuous probability distribution of the observations of the child node for each of the two states of the parent node based on values of observations of the child node for which the state of the parent node is known, and
b) inferring for a new observation of the child node for which the state of the parent node is not known the probability of at least a first state of the two states of the parent node, wherein the inferring includes calculating (i) for the lower-located probability distribution, which is located at the relatively lower location with respect to the values of the observations of the child node, the mass of the portion of the probability distribution being larger than the value of the new observation of the child node and (ii) for the higher-located probability distribution, which is located at the relatively higher location with respect to the values of the observations of the child node, the mass of the portion of the probability distribution being smaller than the value of the new observation of the child node, and calculating the probability of the first state based on the calculated masses.

Since the inferring of the probability of the first state of the two states of the discrete parent node for the new observation of the continuous child node makes use of masses of portions of the probability distributions, wherein the portions depend on a locational relationship of the probability distributions as well as on the value of the new observation of the child node, the probability of the first state of the parent node may be inferred in a way that ensures that the probability of the first state monotonically changes with monotonically changing values of the new observation of the child node. This is advantageous, for instance, in applications such as gene expression classification, were higher expression levels of a gene correlate with a higher likelihood that the gene is being transcribed.

The "location" of a probability distribution of the observations of the child node indicates where the probability distribution is placed or positioned with respect to the values of the observations. For instance, in a diagram in which the values of the observations are given on the abscissa (x-axis) with lower values more to the left and higher values more to the right, the lower-located probability distribution would be placed more to the left, i.e., relatively lower, than the higher-located probability distribution, which would be placed more to the right, i.e., relatively higher. In this specific case, one could also think of the lower-located probability distribution as the left-most probability distribution and one could think of the higher-located probability distribution as the right-most probability distribution.

The term "first state" is used herein to indicate one of the two states of the parent node without implying a particular order of the states. For instance, the first state may be the state of the parent node for which the continuous probability distribution of the observations of the child node is the lower-located probability distribution, i.e., the probability distribution being located at the relatively lower location with respect to the values of the observations, or it may be the state of the parent node for which the continuous probability distribution of the observations of the child node is the higher-located probability distribution, i.e., the probability distribution being located at the relatively higher location with respect to the values of the observations.

Step a), i.e., the step of providing a continuous probability distribution of the observations of the child node for each of the two states of the parent node based on values of observations of the child node for which the state of the parent node is known can include the actual calibration, i.e., the estimation of the continuous probability distributions based on the values of the observations of the child node for which the state of the parent node is known. Alternatively, the calibrating may already have occurred during an earlier phase (e.g., a research phase) and step a) may only include the providing of the already calibrated Bayesian network for performing step b), i.e., the step of inferring for a new observation of the child node for which the state of the parent node is not known the probability of at least a first state of the two states of the parent node.

It is preferred that the calculation of the masses includes determining which of the probability distributions is the lower-located probability distribution and which is the higher-located probability distribution based on a location parameter of the probability distributions, for instance, a mean value or a median value. For instance, if the mean value is chosen as the location parameter, the lower-located probability distribution is the probability distribution having the smaller mean value and the higher-located probability distribution is the probability distribution having the larger mean value. Likewise, if the median value is chosen as the location parameter, the lower-located probability distribution is the probability distribution having the smaller median value and the higher-located probability distribution is the probability distribution having the larger median value.

It is preferred that the calculation of the probability of the first state includes normalizing one of the calculated masses by the sum of the calculated masses. This allows normalizing the calculated probability of the first state such that it adds up to 1 with the probability of the second state of the two states of the parent node.

It is further preferred that the inferring of the probability of the first state further includes transforming the calculated probability of the first state, wherein the transformation depends on a measure of similarity of the probability distributions. The underlying idea here is that for similar probability distributions, e.g., for probability distributions that are not statistically significantly different, the calculated probability of the first state—and, thus, also of the second state—should be substantially equal to 50%, regardless of the value of the new observation of the child node. This desired behavior can be achieved by means of a suitable transformation that depends on a measure of how different the probability distributions are.

It is preferred that the transformation includes scaling the calculated probability of the first state and applying an offset to it. This allows for a simple way of transforming the calculated probability of the first state to achieve the desired behavior, for instance, to ensure that for probability distributions that are not statistically significantly different, the calculated probabilities of the first state—and, thus, also of the second state—is substantially equal to 50%

It is further preferred that the scaling includes performing a comparison of the probability distributions or of the observations of the child node on which the probability distributions are based to determine the measure of similarity and scaling the calculated probability of the first state in dependence of a function of the determined measure of similarity. For instance, the comparison can be a statistical test, for instance, a two-sample t-test that compares the mean values of the probability distributions or a (non-parametric) Wilcoxon rank-sum test or a Kolmogorov-Smirnov test that compares two cumulative distribution functions. The measure of similarity of the probability distributions may then be a p-value provided by such statistical test or any other score that indicates how similar the probability distributions are.

In one embodiment, the function of the measure of similarity preferably is a linear function thereof.

In another embodiment, the function of the measure of similarity preferably is a non-linear function thereof, preferably, a Hill function.

Preferably, the parent node has further states, wherein in step a) the probability is provided for each of the states of the parent node, wherein in step b) the masses are calculated for successive pairs of the states of the parent node and the probability of the first state is calculated based on the calculated masses.

It is further preferred that the calculation of the probability of the first state includes calculating the odds between successive states of the parent node based on the calculated masses for the states.

It is preferred that the probability of the first state is calculated based on a product of the calculated odds.

In another aspect of the present invention, a Bayesian inference device for performing Bayesian inference in a Bayesian network, which includes a continuous child node and its discrete parent node having two states, is presented, wherein the Bayesian inference device comprises:

a providing unit for providing a continuous probability distribution of the observations of the child node for each of the two states of the parent node based on values of observations of the child node for which the state of the parent node is known, and an inferring unit for inferring for a new observation of the child node for which the state of the parent node is not known the probability of at least a first state of the two states of the parent node, wherein the inferring includes calculating (i) for the lower-located probability distribution, which is located at the relatively lower location with respect to the values of the observations of the child node, the mass of the portion of the probability distribution being larger than the value of the new observation of the child node and (ii) for the higher-located probability distribution, which is located at the relatively higher location with respect to the values of the observations of the child node, the mass of the portion of the probability distribution being smaller than the value of the new observation of the child node, and calculating the probability of the first state based on the calculated masses.

In another aspect of the present invention a computer program for performing Bayesian inference in a Bayesian network, which includes a continuous child node and its discrete parent node having two states, is presented, the computer program comprising program code means for causing a computer to carry out the computer-implemented Bayesian inference method as defined in claim 1, when the computer program is run on the computer.

In another aspect of the present invention a method for inferring activity of a cellular signaling pathway using probabilistic modelling of target gene expressions is presented, wherein the method comprises:

inferring the activity of the cellular signaling pathway in a medical subject based at least on expression levels of one or more target gene(s) of the cellular signaling pathway measured in an extracted sample of the medical subject, wherein the inferring comprises:

determining an activity level of a transcription factor element in the extracted sample of the medical subject, the transcription factor element controlling transcription of the one or more target gene(s) of the cellular signaling pathway, the determining being based at least in part on evaluating a Bayesian network relating expression levels of the one or more target gene(s) of the cellular signaling pathway to the activity level of the transcription factor element;

inferring the activity of the cellular signaling pathway in the medical subject based on the determined activity level of the transcription factor element in the extracted sample of the medical subject, wherein the computer-implemented Bayesian inference method as defined in claim 1 is applied in the evaluation of the Bayesian network.

It is preferred that the method further comprises:

determining whether the cellular signaling pathway is operating abnormally in the medical subject based on the inferred activity of the cellular signaling pathway in the medical subject.

It is also preferred that the method further comprises:

recommending prescribing a drug for the medical subject that corrects for the abnormal operation of the cellular signaling pathway, wherein the recommending is performed if the cellular signaling pathway is determined to be operating abnormally in the medical subject based on the inferred activity of the cellular signaling pathway.

It shall be understood that the computer-implemented Bayesian inference method of claim 1, the Bayesian inference device of claim 11, the computer program of claim 12, and the method of claim 13 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
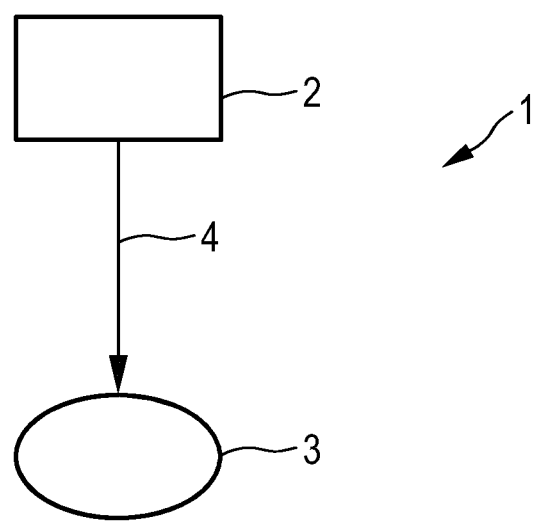
FIG. 1 shows schematically and exemplarily a graphical representation of a simple Bayesian network.
Figure 2:
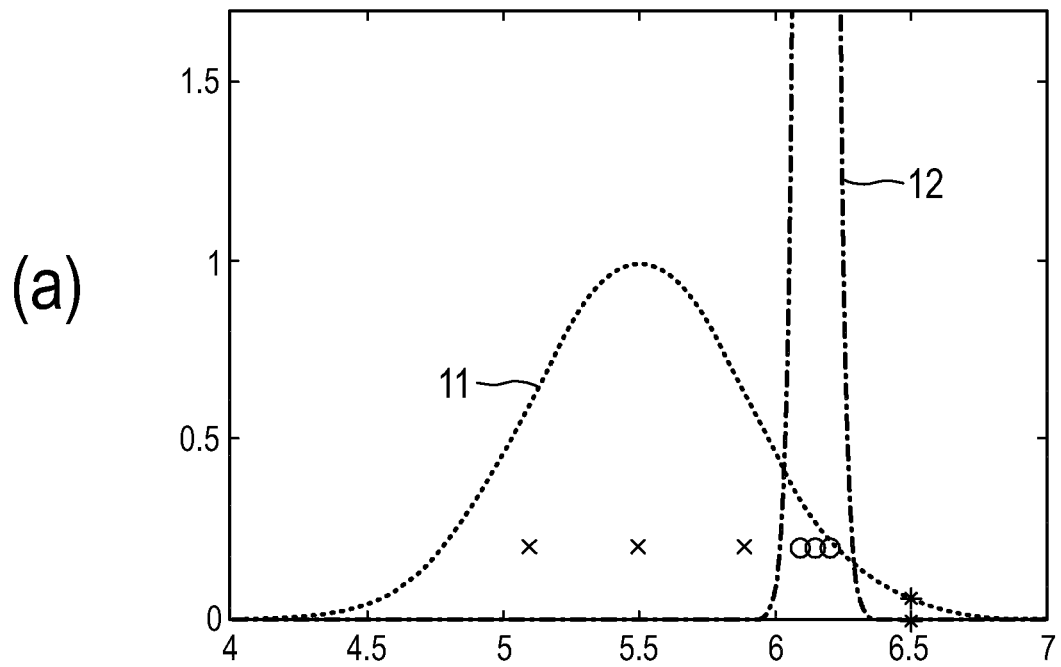
FIG. 2(a) shows schematically and exemplarily the result of calibrating the Bayesian network of FIG. 1 with values of observations of the child node for which the state of the parent node is known.
FIG. 2(b) shows schematically and exemplarily the probability that the state of the parent node is 'State 2' in dependence of the value of the new observation when the standard continuous Bayesian network inference is used.
Figure 2:
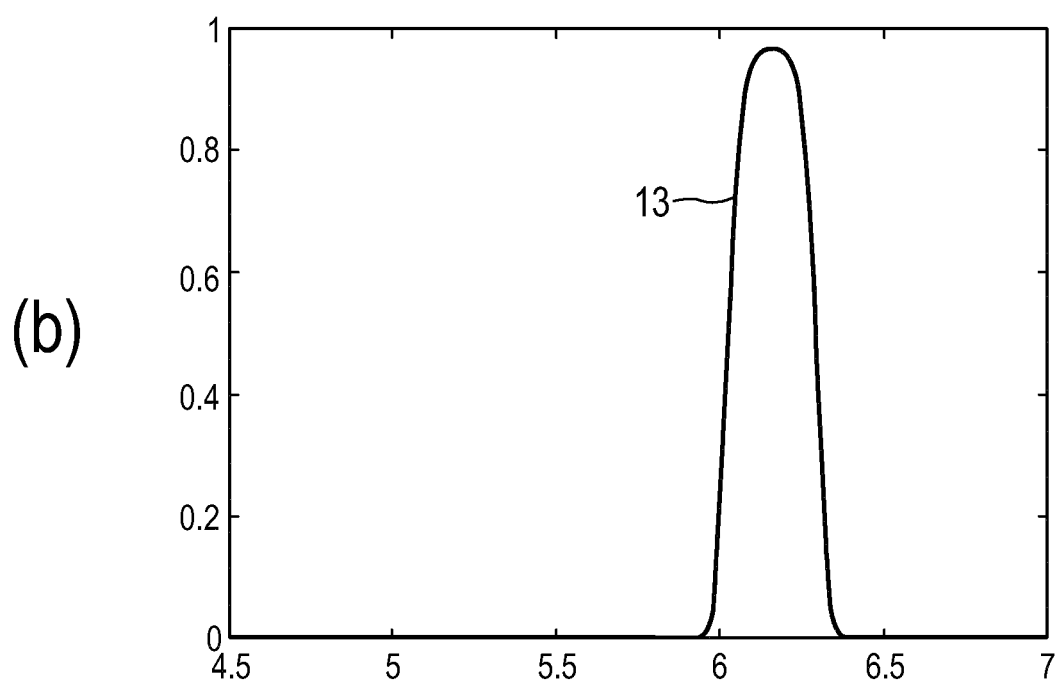

FIG. 1 shows schematically and exemplarily a graphical representation of a simple Bayesian network 1. The Bayesian network 1 is a directed acyclic graph (DAG), which includes two nodes 2 and 3 in a parent/child relationship. An edge 4 that is directed from the parent node 2 to the child node 3 connects the two nodes 2 and 3. The child node 3 is a continuous node that represents continuous observations and the parent node 2 is a discrete node having two states. Provided that no knowledge of the state S of the parent node 2 is available, we assume prior probabilities $P[S=\text{'State } 1\text{'}]=P[S=\text{'State } 2\text{'}]=0.5$. FIG. 2(a) shows schematically and exemplarily the result of calibrating the Bayesian network 1 of FIG. 1 with values of observations of the child node 3 for which the state of the parent node 2 is known. In the graph, the marks 'x' and 'o' indicate the values of the observations of the child node 3 for which the state of the parent node 2 is known to be 'State 1' and 'State 2', respectively. The calibration estimates the probability distribution of the child node 3 for each of the two states 'State 1' and 'State 2' of the parent node 2 from the values of the observations by a continuous distribution. Here, a normal distribution having a mean value μ and a standard deviation σ is used in the estimation. The values of the observations are given on the abscissa (x-axis) and the probability density values given by the probability distributions 11 and 12 are given on the ordinate (y-axis).

As can be seen from the graph, the estimated probability distribution 11 of the child node 3 for which the state of the parent node 2 is known to be 'State 1' is rather broad, i.e., it has a rather large standard deviation $\sigma^{S1}$. In comparison, the estimated probability distribution 12 of the child node 3 for which the state of the parent node 2 is known to be 'State 2' is rather narrow, i.e., it has a rather small standard deviation $\sigma^{S2}$. FIG. 2(a) further shows a new observation of the child node for which the state of the parent node is not known. This new observation is indicated by the mark '*'.

Now, if the probability densities given by the probability distributions 11 and 12 are directly used to infer whether given the new observation the parent node 2 more likely has 'State 1' or 'State 2', one finds that the probability density value given by the probability distribution 11 for the value of the new observation is larger than the probability density value given by the probability distribution 12 for this value. As a result, the standard continuous Bayesian network inference will conclude that given the new observation the state of the parent node 2 is more likely 'State 1' than 'State 2'. This appears to be at odds with the fact that in this example, the value of the new observation is larger than the values of all observations used for the calibration and all calibration data for 'State 2' is larger than the calibration data for 'State 1'.

FIG. 2(b) shows schematically and exemplarily the probability 13 that the state of the parent node 2 is 'State 2' in dependence of the value of a new observation when the standard continuous Bayesian network inference is used. The value of the new observation is given on the abscissa (x-axis) and the probability 13 that the state of the parent node 2 is 'State 2' is given on the ordinate (y-axis). As can be seen from the graph, the probability 13 is not monotonically increasing with the value of the new observation. Rather it has the shape of a narrow bell that steeply increases over a small range of values of the new observation (in this example, from about 5.95 to about 6.15) but then again steeply decreases with higher values of the new observation (in this example, from about 6.15 to about 6.35).

In view of the above, the invention foresees an improved Bayesian inference that ensures that the probability of the state of the parent node 2 monotonically changes with monotonically changing values of the new observation of the child node 3.

To this end, instead of directly using the probability densities given by the probability distributions 11 and 12, masses of portions of the probability distributions 11 and 12 are used to infer for the new observation of the child node 3 the probability of at least a first state, e.g., 'State 2', of the two states of the parent node 2. This is explained in more detail with reference to FIG. 3(a), which shows schematically and exemplarily the use of masses in the situation shown in FIG. 2(a).

As can be seen from the graph, the inferring includes calculating (i) for the lower-located probability distribution, which is located at the relatively lower location with respect to values of the observations of the child node 3, here, the probability distribution 11, the mass 21 of the portion of the probability distribution being larger than the value of the new observation of the child node and (ii) for the higher-located probability distribution, which is located at the relatively higher location with respect to the values of the observations of the child node, here, the probability z-b-distribution 12, the mass 22 of the portion of the probability distribution being smaller than the value of the new observation of the child node. The probability of the first state is then calculated based on the calculated masses 21 and 22. In particular, the calculation of the probability of the first state, here 'State 2', includes normalizing one of the calculated masses 21 and 22 by the sum of the calculated masses 21 and 22.

More formally, assuming that $D^{S1} \sim N(\mu^{S1}, \sigma^{S1})$ and $D^{S2} \sim N(\mu^{S2}, \sigma^{S2})$ represent the probability distributions 11 and 12, respectively, that $\mu^{S1} < \mu^{S2}$, and that m is the new observation, the mass 21 can be calculated as:

$$\alpha \equiv P[D^{S1} > m] = 1 - \Phi((m - \mu^{S1})/\sigma^{S1}),$$

where $\Phi(\cdot)$ denotes the standard normal cumulative distribution function (CDF). Similarly, the mass 22 can be calculated as:

$$\beta \equiv P[D^{S2} < m] = \Phi((m - \mu^{S2})/\sigma^{S2}).$$

The probability that given the new observation m the parent node 2 has the first state, here 'State 2', can then be calculated as:

$$P[S = \text{'State 2'} | m] = \beta / (\alpha + \beta).$$

From this, the probability that given the new observation m the parent node 2 has the other state, here 'State 1', can then be calculated as:

$$P[S = \text{'State 1'} | m] = 1 - P[S = \text{'State 2'} | m].$$

Of course, one can also first calculate the probability that given the new observation m the parent node 2 has 'State 1' as:

$$P[S = \text{'State 1'} | m] = \alpha / (\alpha + \beta),$$

and can then calculate the probability that given the new observation m the parent node 2 has 'State 2' as:

$$P[S = \text{'State 2'} | m] = 1 - P[S = \text{'State 1'} | m].$$

Note that in the above scheme, probabilities can become arbitrarily close to 0 or to 1. In Bayesian networks with discrete nodes, such extreme values are typically avoided because of their strong effect on the inference result. This is done, for example, by adding so-called 'dummy counts'. If, like in the example described with reference to FIG. 2(a) above, there are n=3 calibration samples for each of the two states of the parent node 2, then adding such a dummy count of 1 for both states will limit the inferred probabilities from below by $1/(n+2)$, and from above by $(n+1)/(n+2)$. To avoid extreme probabilities in the present invention, one may clip the calculated probabilities to stay between these values.

Alternatively, one can first calculate $p_1 = \alpha/(\alpha+\beta)$ and $p_2 = \beta/(\alpha+\beta)$ and subsequently calculate:

$$P[S = \text{'State 1'} | m] = (n \cdot p_1 + 1)/(n+2), \text{ and}$$

$$P[S = \text{'State 2'} | m] = (n \cdot p_2 + 1)/(n+2).$$

It is noted that also in this case the probabilities add-up to 1, since $p_1$ and $p_2$ add-up to 1. Moreover, a monotonic behavior is maintained, since the function $f(x) = (n \cdot x + 1)/(n+2)$ is a monotonic—actually even linear—function.

Figure 3:
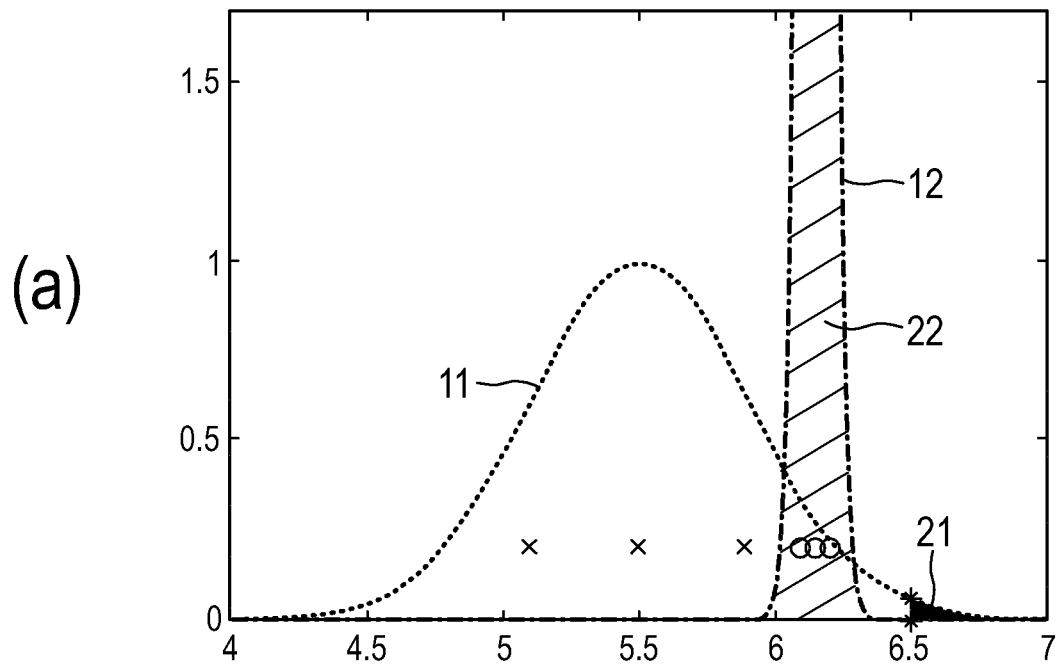
FIG. 3(a) shows schematically and exemplarily the use of masses in the situation shown in FIG. 2(a)
FIG. 3(b) shows schematically and exemplarily the probability that the state of the parent node is 'State 2' in dependence of the value of the new observation when the improved Bayesian network inference is used.
Figure 3:
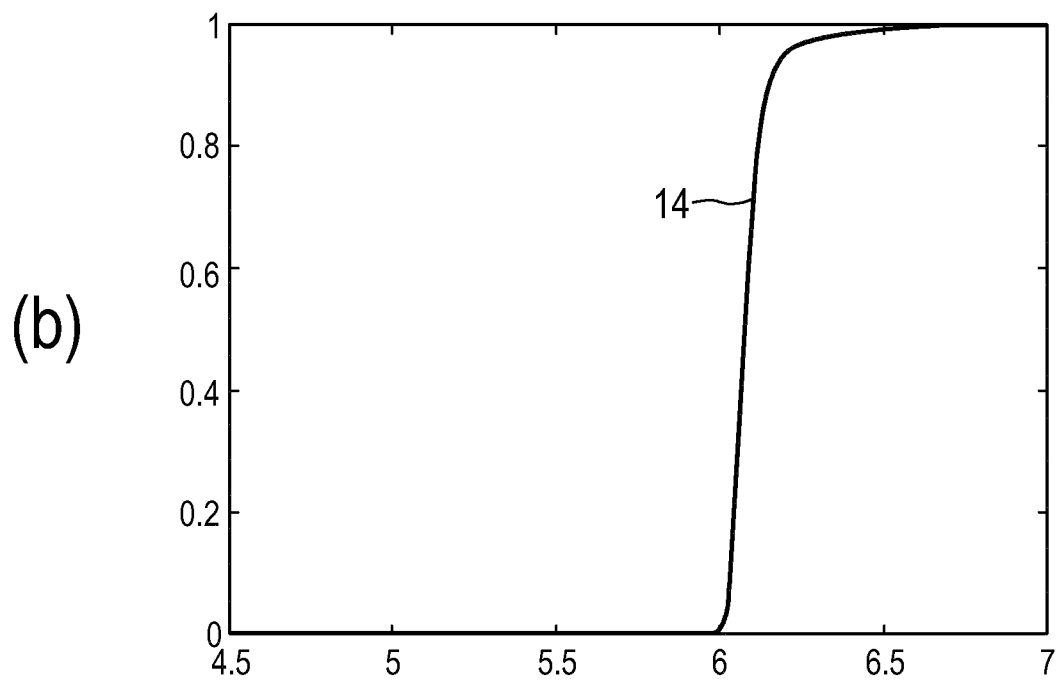

FIG. 3(b) shows schematically and exemplarily the probability 14 that the state of the parent node 2 is 'State 2' in dependence of the value of a new observation when the improved Bayesian network inference is used. As in FIG. 2(b), the value of the new observation is given on the abscissa (x-axis) and the probability 14 that the state of the parent node 2 is 'State 2' is given on the ordinate (y-axis). As can be seen from the graph, the probability 14 is monotonically increasing with the value of the new observation (in this example, starting at about 6.0), wherein the probability 14 saturates to a value of 1 for larger values of the new observation.

Figure 4:
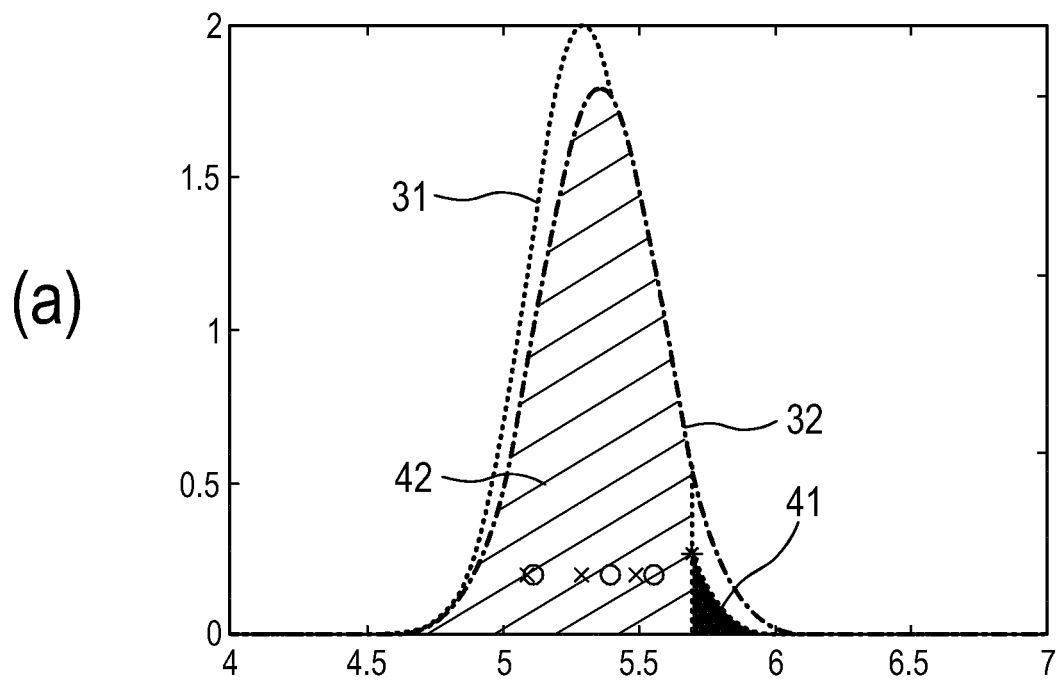
FIG. 4(a) shows schematically and exemplarily the use of masses in a situation where the calibration data are almost the same for the two states of the parent node.
FIG. 4(b) shows schematically and exemplarily the probability that the state of the parent node is 'State 2' in dependence of the value of the new observation in the case of FIG. 4(a)
Figure 4:
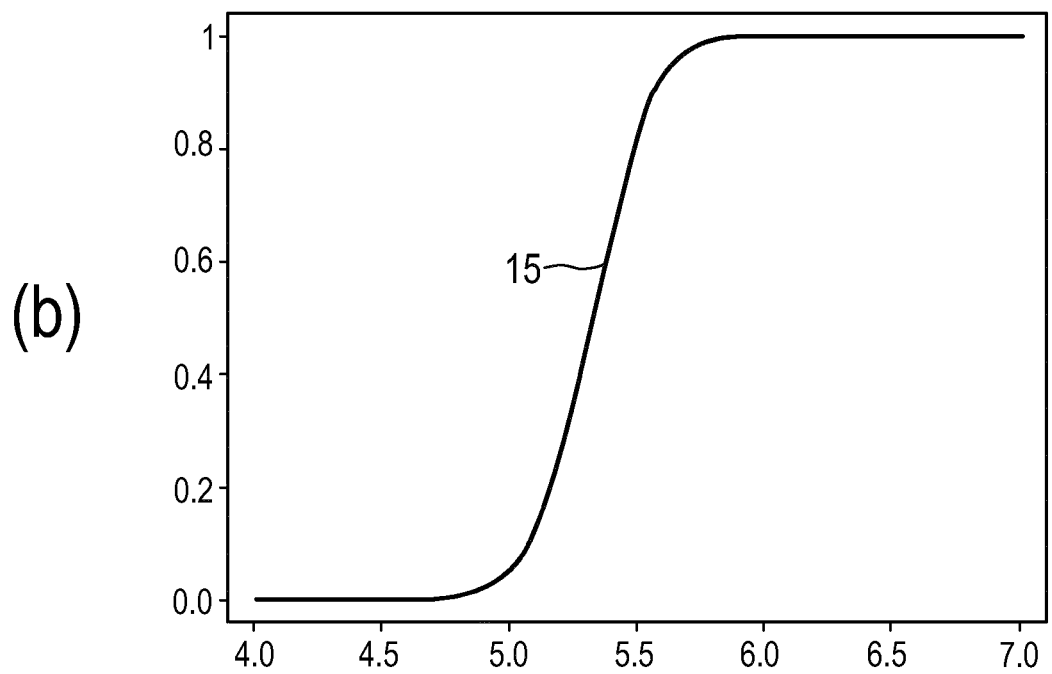

The above-described improved computer-implemented Bayesian inference method may still have drawbacks when the calibration data for the two states of the parent node 2 are nearly identical. In this case, it would be desired that the calculated probabilities are close to 50%-50% for the likelihood that the state of the parent node 2 is either 'State 1' or 'State 2', regardless of the value of the new observation. The mass-based Bayesian inference of the probabilities described so far does not comply with this condition. This will be illustrated with reference to FIG. 4(a), which shows schematically and exemplarily the use of masses in a situation where the calibration data are almost the same for the two states of the parent node 2 (here, 5.1, 5.3 and 5.5 for 'State 1' as well as 5.12, 5.4 and 5.56 for 'State 2'). As in FIG. 2(a), the marks 'x' and 'o' indicate the values of the observations of the child node 3 for which the state of the parent node 2 is known to be 'State 1' and 'State 2', respectively, and the calibration estimates the probability distribution of the child node 3 for each of the two states 'State 1' and 'State 2' of the parent node 2 from the values of the observations by a normal distribution having a mean value $\mu$ and a standard deviation $\sigma$. The values of the observations are given on the abscissa (x-axis) and the probability density values given by the probability distributions 31 and 32 are given on the ordinate (y-axis).

As can be seen from the graph, the estimated probability distribution 31 of the child node 3 for which the state of the parent node 2 is known to be 'State 1' is similar to the estimated probability distribution 32 of the child node 3 for which the state of the parent node 2 is known to be 'State 2', i.e., they have similar mean values $\mu^{S1}$ and $\mu^{S2}$ and standard deviations $\sigma^{S1}$ and $\sigma^{S2}$, wherein $\mu^{S1}$ is, however, slightly smaller than $\mu^{S2}$. FIG. 4(a) then further shows a new observation of the child node for which the state of the parent node is not known. This new observation is indicated by the mark '*'.

Now, if the mass-based Bayesian inference is used to infer whether given the new observation the parent node 2 more likely has 'State 1' or 'State 2', one finds that by calculating (i) for the lower-located probability distribution, which is located at the relatively lower location with respect to the values of the observations of the child node, here, the probability distribution 31, the mass 41 of the portion of the probability distribution being larger than the value of the new observation of the child node 3 and (ii) for the higher-located distribution, which is located at the relatively higher location with respect to the values of the observations of the child node, here, the probability distribution 32, the mass 42 of the portion of the probability distribution being smaller than the value of the new observation of the child node, the mass 41 is much smaller than the mass 42, which has the effect that the computed probability that the state of the parent node 2 is 'State 2' is much higher than the probability of 'State 1'. This appears to be at odds with the fact that in this example, the probability distributions 31 and 32 are indeed almost identical.

This is also evidenced by FIG. 4(b), which shows schematically and exemplarily the probability 33 that the state of the parent node 2 is 'State 2' in dependence of the value of a new observation of the child node 3 in the case of FIG. 4(a). As in FIGS. 2(b) and 3(b), the value of the new observation is given on the abscissa (x-axis) and the probability 33 that the state of the parent node 2 is 'State 2' is given on the ordinate (y-axis). As can be seen from the graph, the probability 3 is monotonically increasing with the value of the new observation (in this example, starting at about 5.0), wherein the probability 33 saturates to a value of 1 for larger values of the new observation.

In view of the above, the inferring of the probability of the first state further includes transforming the calculated probability of the first state, here, 'State 2', wherein the transformation depends on a measure of similarity of the probability distributions, here, the probability distributions 31 and 32. As already described above, the underlying idea here is that for similar probability distributions, e.g., for probability distributions that are not statistically significantly different, the probability of the first state—and, thus, also of the second state—should be substantially equal to 50%, regardless of the value of the new observation of the child node 3. In this embodiment, this is achieved by a transformation that includes scaling the calculated probability of the first state and applying an offset to it. Here, the scaling includes performing a two-sample t-test on the values of the observations of the child node 2 on which the probability distributions 31 and 32 are based to determine the measure of similarity, here, the p-value provided by the two-sample t-test, and scaling the calculated probability of the first state in dependence of a function of the determined measure of similarity.

More formally, a suitable transformation can be defined such that:

$$P^T[S=\text{'State 2'}]=0.5+(1-f(p))\cdot(P[S=\text{'State 2'}]-0.5),$$

where $P^T[S=\text{'State 2'}]$ is the transformed probability that given the new observation the state of the parent node 2 is 'State 2', p is the p-value of the two-sample t-test and f is a monotonically increasing function of p.

As described above, the drawback of the improved computer-implemented Bayesian inference method only becomes manifest when there is only a small difference in the mean values $\mu^{S1}$ and $\mu^{S2}$ of the probability distributions 31 and 32 that approximate the probability of each of the two states of the parent node 2. Therefore, the p-value of the two-sample t-test can be used to scale the calculated probabilities: The higher the p-value of the two-sample t-test, the closer are the mean values $\mu^{S1}$ and $\mu^{S2}$ and the closer the calculated probabilities should be to 50%-50%.

In one possible realization, the function of the p-value is a linear function of the p-value. This can be useful when it is desirable that the transformed probability degrades in a linear fashion with the p-value. For instance, the function of the p-value can be $f(p)=p$.

An alternative is to make use of a non-linear function of the p-value in the transformation. For instance, one can use the Hill-function $f(p)=p^n/(C^n+p^n)$, where C and n are parameters that can be defined depending on personal preferences, such as the p-value at which $(P[S=\text{'State 2'}]-0.5)$ is degraded with 50% and the steepness of the curve.

An example of a Hill-function $f(p)$ 50 is shown schematically and exemplarily in FIG. 5(a) for the values C=0.2 and n=4. The p-values of the two-sample t-test between 0 and 1 are given on the abscissa (x-axis) and the values of the Hill-function 50 are given on the ordinate (y-axis).

Figure 5:
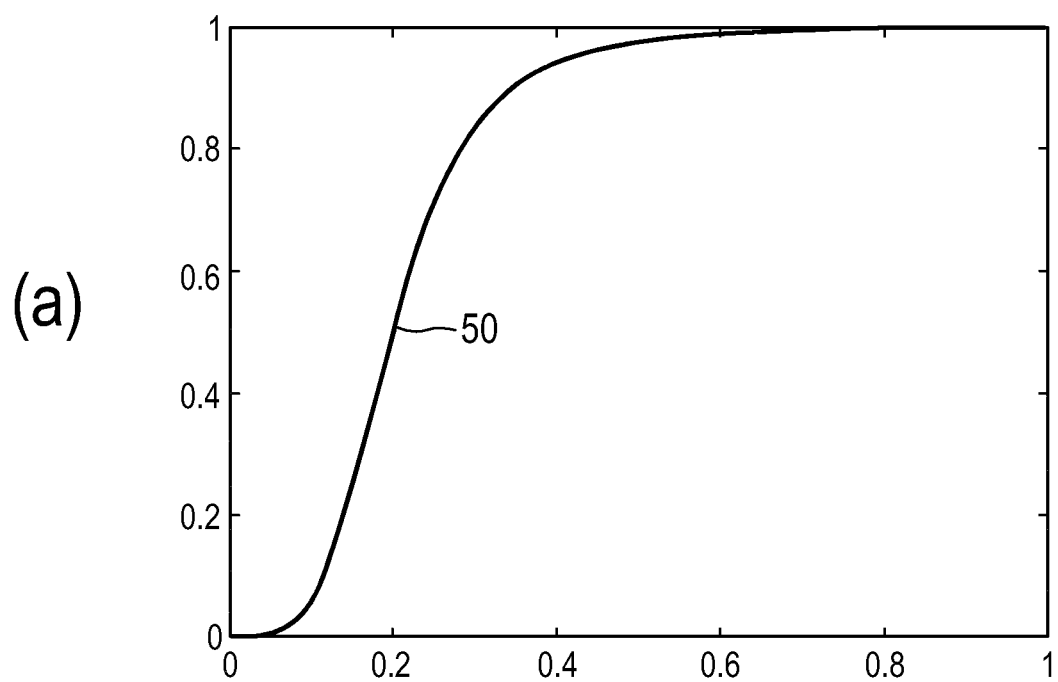
FIG. 5(a) shows schematically and exemplarily an example of a Hill-function $f(p)$ for the values $C=0.2$ and $n=4$.
FIG. 5(b) shows schematically and exemplarily the probability that the state of the parent node is 'State 2' in dependence of the value of the new observation when the improved Bayesian network inference with additional transformation is used.
Figure 5:
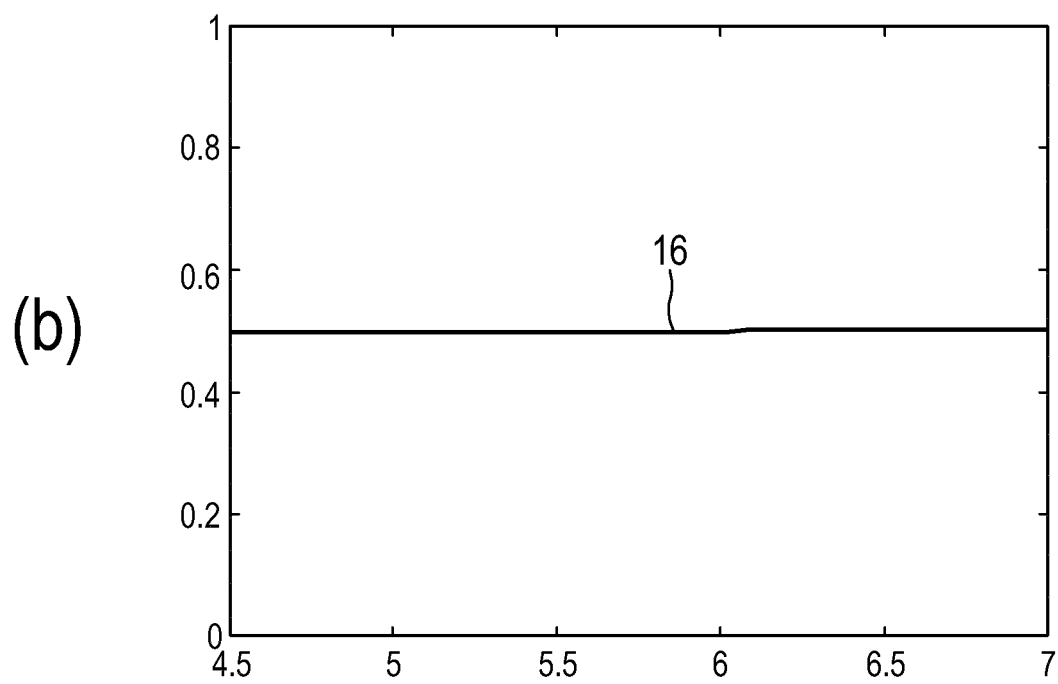

FIG. 5(*b*) shows schematically and exemplarily the probability 16 that the state of the parent node 2 is 'State 2' in dependence of the value of a new observation when the improved Bayesian network inference with additional transformation is used. As in FIGS. 2(*b*) and 3(*b*), the value of the new observation is given on the abscissa (x-axis) and the probability 16 that the state of the parent node 2 is 'State 2' is given on the ordinate (y-axis). As can be seen from the graph, the probability 16 is substantially equal to 50%, regardless of the value of the new observation. The p-value provided by the two-sample t-test for the calibration data of FIG. 4(*a*) is 0.746. (One might argue that in this specific example, one might just as well have ignored the child node 3, as it has practically no effect on the inferred probabilities of the parent node 2. However, the improved computer-implemented Bayesian inference method allows for a graceful ignoring of the child node 3 and its evidence. For instance, if the p-value is around 0.10, the probability distributions are not statistically significantly different, but they may be considered interesting enough to take into account, albeit with a somewhat lower weight, as it is done according to the present invention.

So far, we only described the case where the parent node 2 has only two states 'State 1' and 'State 2'. The improved computer-implemented Bayesian inference method (with or without the additional transformation) can also be extended to the case where the parent node has further states, e.g., where the parent node has three, five or ten states. In this case, the continuous probability distribution of the observations of the child node is estimated for each of the states, e.g., the five states, of the parent node based on the values of the observations of the child node for which the state of the parent node is known. For instance, as described above for the two-state case, a normal distribution having a mean value $\mu$ and a standard deviation $\sigma$ can be used in the estimation, wherein the masses are then calculated for successive pairs of the states of the parent node and the probability of the first state is calculated based on the calculated masses. More formally, assuming that we do not have two but n>2 (discrete) states ('State 1', 'State 2', . . . , 'State n'), that $D^{S1} \sim N(\mu^{S1}, \sigma^{S1})$, $D^{S2} \sim N(\mu^{S2}, \sigma^{S2})$ . . . $D^{Sn} \sim N(\mu^{Sn}, \sigma^{Sn})$ represent the distributions, respectively, that $\mu^{S1} < \mu^{S2} < \ldots < \mu^{Sn}$, and that m is the new observation, we first compare the distributions $D^{S1}$ and $D^{S2}$ to calculate the masses $P[D^{S1}>m]$ and $P[D^{S2}<m]$ for states 'State 1' and 'State 2'. We then calculate the masses $P[D^{S2}>m]$ and $P[D^{S3}<m]$ for states 'State 2' and 'State 3', the masses $[D^{S3}>m]$ and $P[D^{S4}<m]$ for states 'State 3' and 'State 4' and so on up to the masses $P[D^{Sn-1}>m]$ and $P[D^{Sn}<m]$ for states 'State n−1' and 'State n'. Of course, it is not strictly necessary to perform the comparisons in this order, e.g., the comparisons can also be performed starting with the two largest mean values $\mu^{Sn-1}$ and $\mu^{Sn}$ or in any other suitable order.

In this embodiment, the calculation of the probability of the first state, e.g., 'State i', includes calculating the odds between successive states of the parent node based on the calculated masses for the states. In particular, we may calculate the odds $O^{Si+1,Si}$ between successive states 'State i' and 'State i+1' as:

$$O^{Si+1,Si} = P[D^{Si+1}<m]/P[D^{Si}<m], i=1, \ldots, n-1.$$

Based on the above, the probability of the first state, here, 'State i' (which can be any one of the n>2 states of the parent node), is calculated based on a product of the calculated odds. In particular, the probability that the state of the parent node is 'State i', P[S='State i'], can be expressed as a function of P[S='State 1'] as:

$$P[S='\text{State } i'] = P[S='\text{State } 1'] \cdot \Pi_{j=1}^{i-1} O^{Sj+1,Sj}, i=1, \ldots, n,$$

wherein P[S='State 1'] can then be calculated by normalizing the sum of all P[S='State i'] to 1.

The improved computer-implemented Bayesian inference method (with or without the additional transformation) can be applied in all technical fields where Bayesian networks and Bayesian inference are used, for example, bioinformatics, medicine, clinical decision support (CDS) systems and engineering. In the following, we exemplarily describe its application in the field on cellular signaling pathway analysis.

It has been shown that the possibilities of characterizing patients having a tumor, e.g., breast cancer, can be improved by studying effects occurring in the cellular signaling pathway downstream of the HER2 receptor e.g., the PI3K cellular signaling pathway. For this reason, a method for inferring activity of a PI3K cellular signaling pathway using mathematical modelling of target gene expressions has been described in the published international patent application WO 2015/101635 A1 ("Assessment of the PI3K cellular signaling pathway activity using mathematical modelling of target gene expression"). Other cellular signaling pathways have been analyzed using corresponding methods. See, for instance, the published international patent application WO 2016/062891 A1 ("Assessment of TGF-β cellular signaling pathway activity using mathematical modelling of target gene expression") or the published international patent application WO 2017/029215 A1 ("Assessment of NFkB cellular signaling pathway activity using mathematical modelling of target gene expression"). These patent applications foresee different mathematical models, such as models that are based at least in part on one or more linear combination(s) of expression levels of one or more target gene(s) of the cellular signaling pathway or probabilistic models, in particular, Bayesian networks, that are based at least in part on conditional probabilities relating a transcription factor element and expression levels of the one or more target gene(s) of the cellular signaling pathway.

With respect to the Bayesian networks, these patent applications then disclose a method for inferring activity of a cellular signaling pathway, for instance, the PI3K, NFkB or TGF-β cellular signaling pathway, using probabilistic modelling of target gene expressions, wherein the method comprises:

inferring the activity of the cellular signaling pathway in a medical subject based at least on expression levels of one or more target gene(s) of the cellular signaling pathway measured in an extracted sample of the medical subject, wherein the inferring comprises:

determining an activity level of a transcription factor element in the extracted sample of the medical subject, the transcription factor element controlling transcription of the one or more target gene(s) of the cellular signaling pathway, the determining being based at least in part on evaluating a Bayesian network relating expression levels of the one or more target gene(s) of the cellular signaling pathway to the activity level of the transcription factor element; and inferring the activity of the cellular signaling pathway in the medical subject based on the determined activity level of the transcription factor element in the extracted sample of the medical subject.

Here, it is foreseen that the improved computer-implemented Bayesian inference method (with or without the additional transformation) is applied in the evaluation of the Bayesian network.

To illustrate the effects of this, a simple three-layer Bayesian network similar to the one shown in FIG. 1 of W. Verhaegh et al., "Selection of personalized patient therapy through the use of knowledge-based computational models that identify tumor-driving signal transduction pathways", Cancer Research, Vol. 74, No. 11, 2014, pages 2936 to 2945 was used as a simplified model of the transcriptional program of the cellular signaling pathway. The Bayesian network consists of three types of nodes: (i) a discrete transcription complex TC (with states 'absent' and 'present') at the top layer, (ii) discrete target genes $TG_i$ (with states 'down' and 'up') at the middle level, and (iii) and continuous probesets $PS_{i,j}$ (with continuous observations of the probeset intensity) corresponding to target genes at the bottom level. The model describes (i) how the expression of target genes depends on transcription complex activation and (ii) how probeset intensities in turn depend on the expression of the respective target genes. In the model, the target genes are the child nodes of the transcription complex and the probesets are the child nodes of the target genes.

As already mentioned above, when describing the background of the invention, by making use of continuous child nodes, a loss of information due to the otherwise necessary discretization process is avoided. In the context of the probabilistic modelling of cellular signaling pathways, such a discretization can lead to problems in the calibration of a fully discrete model if samples from multiple cell lines are used as calibration data.

Since the cellular signaling pathway model is a simplification of signaling pathway biology and since biologic measurements are typically noisy, a probabilistic Bayesian network approach, meaning that relationships (i) between transcription complex and target genes and (ii) between target genes and their respective probesets are described in probabilistic terms, is in general well suited for the modelling. Furthermore, it is assumed that the oncogenic signaling pathway driving tumor growth is not transiently and dynamically activated, but long term or even irreversibly. Hence, the model was developed for interpretation of a static cellular condition, and complex dynamic pathway features were not incorporated.

Once the Bayesian network model has been built and calibrated for a particular signaling pathway, the model can be used on data of a new tumor sample by entering probeset measurements as observations in the bottom layer, and inferring backwards in the model the activity probability of the transcription complex. Hence, this latter probability is the primary read-out used to indicate cellular signaling pathway activity, which can be translated into odds of the cellular signaling pathway being active by taking the ratio of the probability of it being active versus it being inactive (i.e., the odds are given by p/(1−p) if p is the predicted probability of it being active).

The probabilistic relations of the Bayesian network were made quantifiable based the assumption that the intensity observations of the probesets follow a normal distribution having a mean value μ and a standard deviation σ. The continuous probability distributions were then calibrated on samples for which the status ('active' or 'passive') of the cellular signaling pathway was known in order to infer whether evidence obtained at probeset level indicates an 'active' or 'passive' cellular signaling pathway. In this way, the probability tables between target gene nodes and probeset nodes were calculated, wherein it was assumed that for an upregulated target gene its two states 'up' and 'down' correspond to the states 'active' and 'inactive' of the cellular signaling pathway, respectively. The probabilistic relationships between the top and middle layers of the model, i.e., between the transcription complex and the target genes, were thereby manually set, based on literature knowledge.

In the following, we show results of applying the improved computer-implemented Bayesian inference method (with or without the additional transformation) in the evaluation of the connection between a continuous probeset node and the corresponding discrete target gene node. A newly inferred probability of a target gene being 'up' or 'down' can then be propagated upstream in the Bayesian network for the rest of the inference process that eventually calculates the probability of the cellular signaling pathway being 'active' or 'inactive'.

Figure 6:
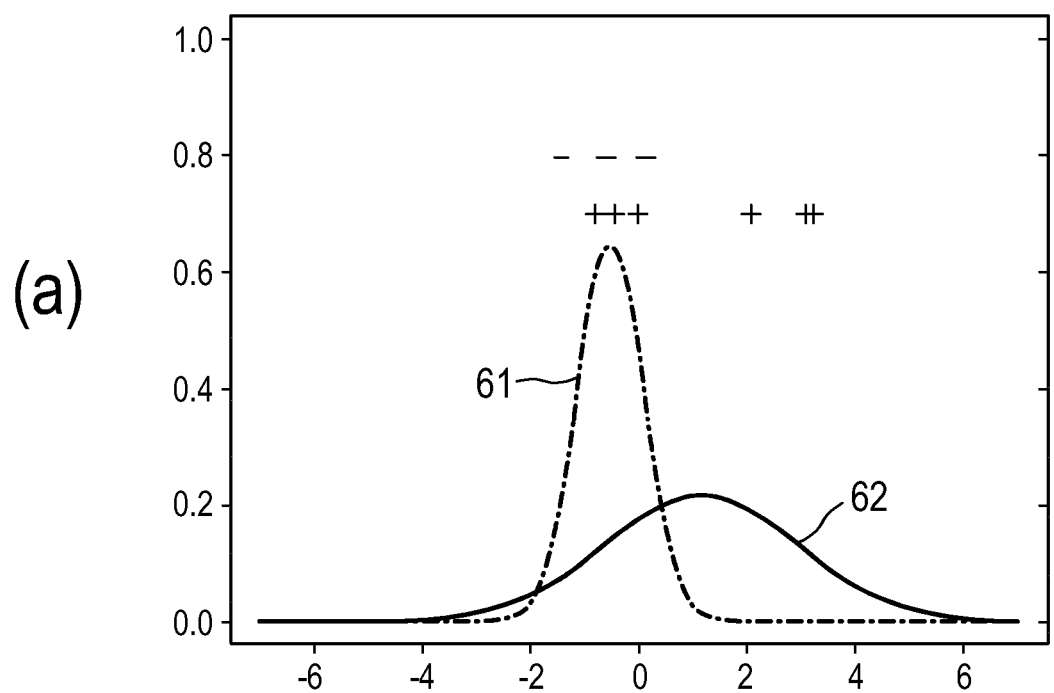
FIG. 6(a) shows schematically and exemplarily the calibration data for a target gene TARG1 (parent node) with intensity observations from a probeset TARG1-PS (child node) for samples from an in-house dataset for which the state of the target gene node is known.
FIG. 6(b) shows schematically and exemplarily the probability that the state of the parent node (i.e., target gene TARG1) is 'up' in dependence of the value of a new observation (i.e., probeset intensities for samples from a new dataset) when the standard continuous Bayesian network inference vs. the improved Bayesian inference is used.
Figure 6:
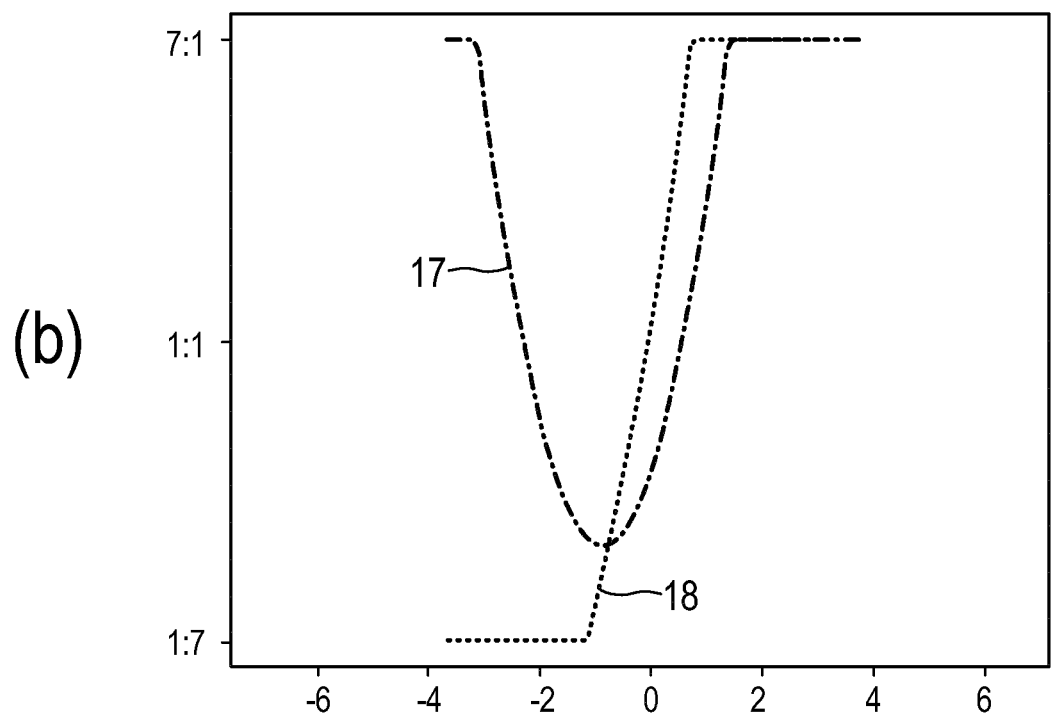

FIG. 6(a) shows schematically and exemplarily the calibration data for a target gene TARG1 (parent node) with intensity observations from a probeset TARG1-PS (child node) for samples from an in-house dataset for which the state of the target gene node is known. In the graph, the marks '+' and '−' indicate the values of the intensity observations of the child node for which the state of the parent node, i.e., the target gene TARG1, is known to be 'up' and 'down', respectively. The values of the intensity observations are given on the abscissa (x-axis) and the probability density values given by the probability distributions 61 and 62 are given on the ordinate (y-axis).

As can be seen from the graph, the estimated probability distribution 61 of the child node for which the state of the parent node is known to be 'down' is rather narrow, i.e., it has a rather small standard deviation $\sigma^{down}$. In comparison, the estimated probability distribution 62 of the child node for which the state of the parent node is known to be 'up' is rather broad, i.e., it has a rather large standard deviation $\mu^{up}$. Regarding the mean values, it can be seen that the probability distribution 61 has a smaller mean value $\mu^{down}$ compared to the mean value $\mu^{up}$ of the probability distribution 62. Using the mean value as the location parameter, it can then be determined that the probability distribution 61 is the lower-located probability distribution and the probability distribution 62 is the higher-located probability distribution.

FIG. 6(b) shows schematically and exemplarily the probability that the state of the parent node (i.e., the target gene TARG1) is 'up' in dependence of the value of a new observation (i.e., probeset intensities for samples from a new dataset) when the standard continuous Bayesian network inference vs. the improved Bayesian inference is used. The value of the new observation is given on the abscissa (x-axis) and the odds that the state of the parent node is 'up' is given on the ordinate (y-axis). Here, the probability p has been calculated with additional 'dummy counts', as explained in more detail above, and the figure shows the odds p/(1−p) of the target gene TARG1 being 'up'. As can be seen from the graph, with the standard continuous Bayesian network inference the odds 17 are not monotonically increasing with the value of the new observation. Rather they have the shape of an inverted bell that decreases over a range of values of the new observation (in this example, from about −3 to about −0.75) but then again steeply increases with higher values of the new observation (in this example, from about −0.75 to about +1.5). In contrast, with the improved Bayesian network the odds 18 are monotonically increasing with the value of the new observation (in this example, starting at about −1 to about +1).

Figure 7:
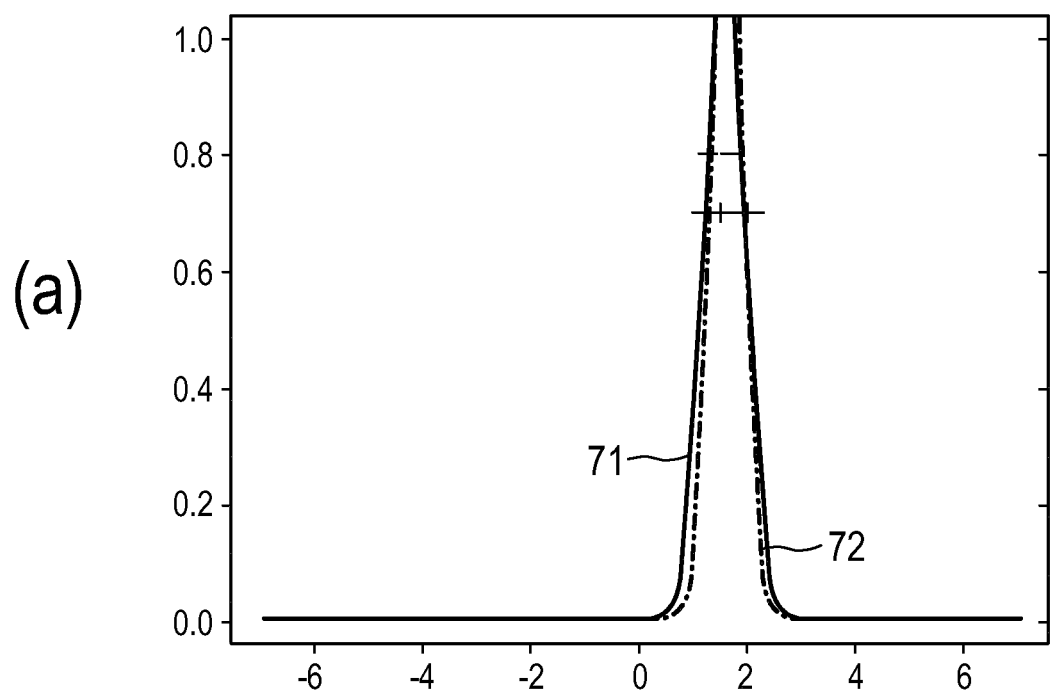
FIG. 7(a) shows schematically and exemplarily a situation where the calibration data are almost the same for the two states of the parent node. Here, the parent node is a target gene TARG2 which has been calibrated with intensity observations from a probeset TARG2-PS (child node) for samples from another in-house dataset for which the state of the target gene node is known.
FIG. 7(b) shows schematically and exemplarily the probability that the state of the parent node (i.e., target gene TARG2) is 'up' in dependence of the value of a new observation of the child node (i.e., probeset intensities for samples from a new dataset) in the case of FIG. 7(a) when the standard continuous Bayesian network inference vs. the improved Bayesian inference without the additional transformation is used.
Figure 7:
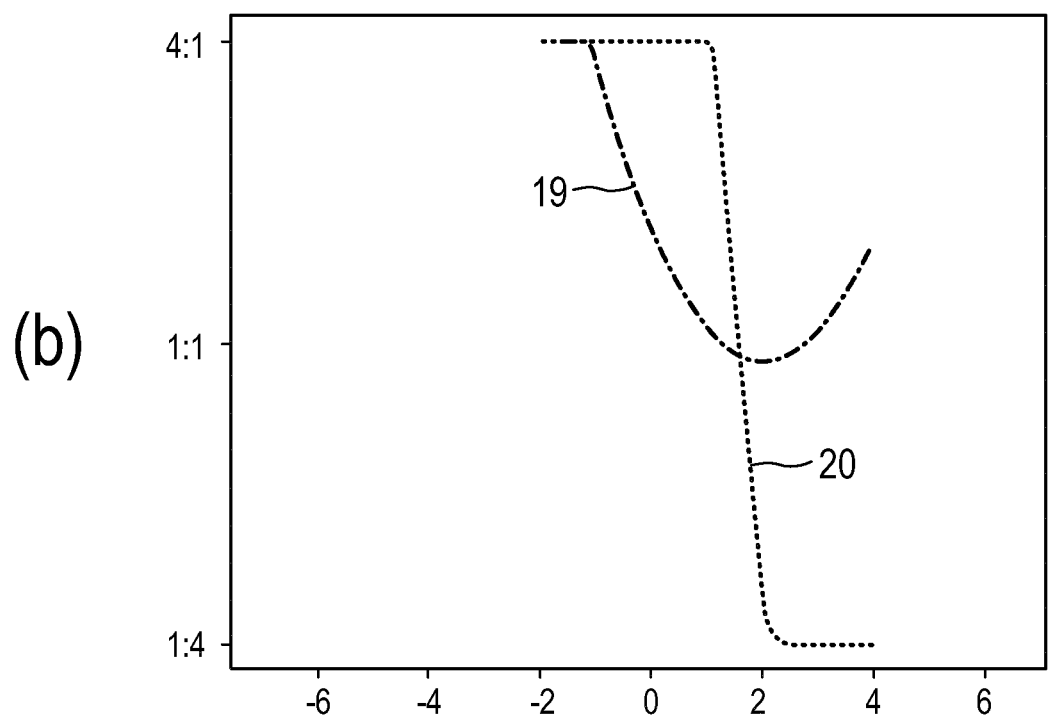

FIG. 7(a) shows schematically and exemplarily a situation where the calibration data are almost the same for the two states of the parent node (the p-value as calculated by the two-sample t-test is 0.867). Here, the parent node is another target gene TARG2 which has been calibrated with intensity observations from a probeset TARG2-PS (child node) for samples from an in-house dataset for which the state of the target gene node is known. In the graph, the marks '+' and '−' indicate the values of the intensity observations of the child node for which the state of the parent node, i.e., the target gene TARG2, is known to be 'up' and 'down', respectively. The values of the intensity observations are given on the abscissa (x-axis) and the probability density values given by the probability distributions 71 and 72 are given on the ordinate (y-axis).

As can be seen from the graph, the estimated probability distribution 71 of the child node for which the state of the parent node is known to be 'down' is similar to the estimated probability distribution 72 of the child node for which the state of the parent node is known to be 'up', i.e., they have similar mean values $\mu^{down}$ and $\mu^{up}$ and standard deviations $\sigma^{down}$ and $\sigma^{up}$.

FIG. 7(b) shows schematically and exemplarily the probability that the state of the parent node (i.e., target gene TARG2) is 'up' in dependence of the value of a new observation of the child node (i.e., probeset intensities for samples from a new dataset) in the case of FIG. 7(a) when the standard continuous Bayesian network inference vs. the improved Bayesian inference without the additional transformation is used. As in FIG. 6(b), the value of the new observation is given on the abscissa (x-axis) and the odds that the state of the parent node is 'up' is given on the ordinate (y-axis). As can be seen from the graph, neither for the standard continuous Bayesian network inference nor for the improved Bayesian inference without the additional transformation, the odds 19 resp. 20 reflect the fact that the probability distributions 71 and 72 are indeed almost identical, wherefore the odds of the target gene TARG2 being 'up'—and, thus, also of it being 'down'—should be substantially equal to 50%, regardless of the value of the new observation of the child node.

Figure 8:
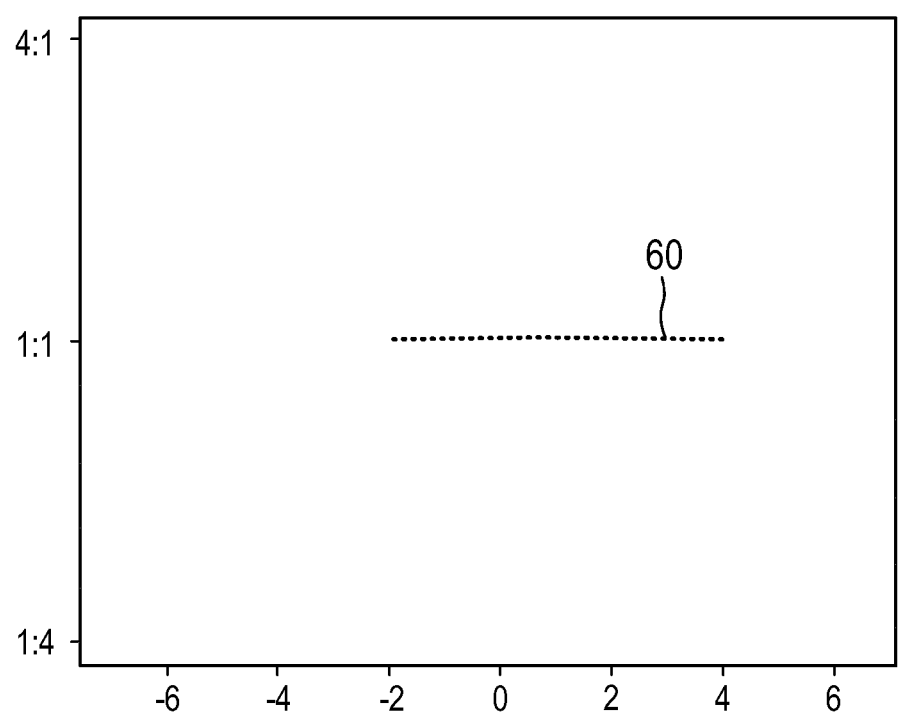
FIG. 8 shows schematically and exemplarily that the odds shown in FIG. 7(b) can be fixed using the Hill function.

FIG. 8 shows schematically and exemplarily that the odds 20 shown in FIG. 7(b) can be fixed using the Hill function, as described above. The value of the new observation is given on the abscissa (x-axis) and the probability that the state of the parent node is 'up'—calculated with additional 'dummy counts' and represented as the odds p/(1−p) of the target gene TARG2 being 'up' transformed by the Hill function—is given on the ordinate (y-axis). As can be seen from the graph, for the improved Bayesian inference, the additional transformation with the Hill function leads to odds 60 that the state of the parent node (i.e., target gene TARG2) is 'up' that are substantially equal to 50%, as desired.

Figure 9:
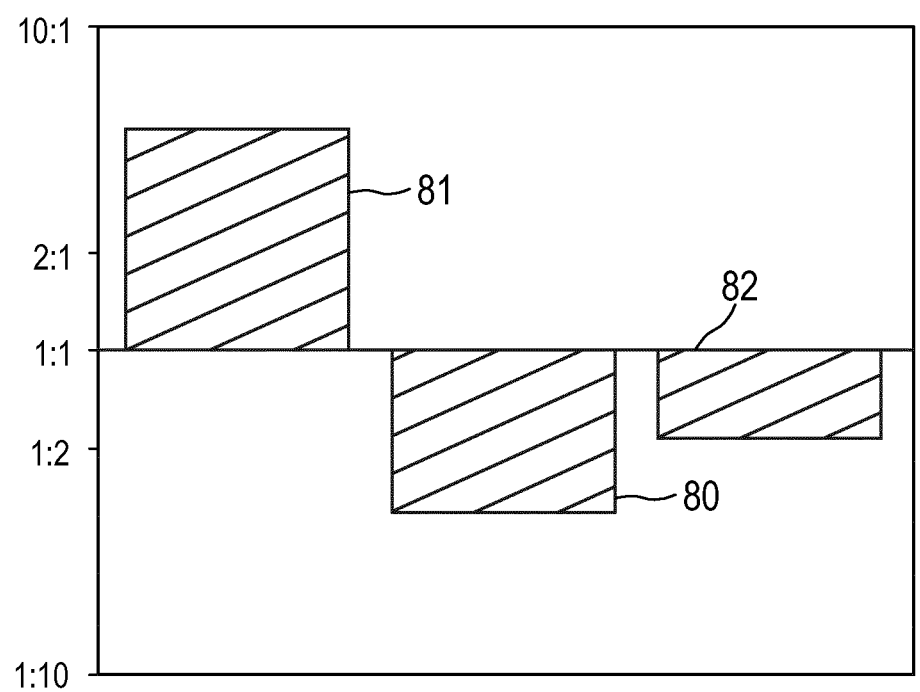
FIG. 9 shows schematically and exemplarily how the improved computer-implemented Bayesian inference method compares to the conventional continuous Bayesian inference method.

The problems with the conventional continuous Bayesian inference are further illustrated in FIG. 9, which schematically and exemplarily shows how the improved computer-implemented Bayesian inference method compares on the above-outlined three-layer Bayesian network of W. Verhaegh et al. Here, the model was based on three target genes and was calibrated with real calibration samples. Next, the expression levels of a real sample with an inactive cellular signaling pathway was used as evidence in the model, after which the probability of the cellular signaling pathway being in the state 'active' was calculated. The result should indicate an inactive cellular signaling pathway and as can be seen from block 80 in FIG. 9, the odds calculated by the improved computer-implemented Bayesian inference method indeed indicate an inactive cellular signaling pathway. In contrast, the conventional continuous Bayesian inference method incorrectly indicates an active cellular signaling pathway (see block 81), because the continuous probability distributions are not monotonically increasing. A discrete version of the model also indicates an inactive cellular signaling pathway (see block 82), but due to the loss of information in the discretization process the odds are lower compared to the improved computer-implemented Bayesian inference method.

These experimental results all illustrate that the identified problems with the conventional continuous Bayesian inference indeed occur in applications such as, for instance, gene expression classification, were higher expression levels of a gene correlate with a higher likelihood that the gene is being transcribed.

By using the described method for inferring activity of a cellular signaling pathway using probabilistic modelling of target gene expressions, wherein the improved computer-implemented Bayesian inference method (with or without the additional transformation) is applied in the evaluation of the Bayesian network, the activity of the cellular signaling pathway may be inferred in a more reliable manner.

The inferred activity of the cellular signaling pathway in a medical subject can then be used as a basis for determining whether the cellular signaling pathway is operating abnormally in the medical subject. If the cellular signaling pathway is operating abnormally in the medical subject, a drug can be prescribed for the medical subject that corrects for the abnormal operation of the cellular signaling pathway.

For instance, in breast cancer, Wnt activity was detected by the described Bayesian network model in around one third of triple-negative or basal-type samples, which agrees with available evidence on a role for Wnt activity in this breast cancer subtype (cf., for instance, F. C. Geyer, "β-Catenin pathway activation in breast cancer is associated with triple-negative phenotype but not with CTNNB1 mutation", Modern Pathology, Vol. 24, 2011, pages 209 to 231). In only very rare cases of breast cancer, a potentially Wnt-activating gene mutation has been found, suggesting that Wnt activity is most likely induced by paracrine interactions between cancer cells and their microenvironment. With a number of Wnt-targeting drugs in the pipeline of pharmaceutical companies, development of a reliable test to identify Wnt pathway activity in this cancer subtype with highly unfavorable prognosis is considered high priority, as β-catenin staining is not reliable enough to indicate Wnt pathway activity. Analysis of transcriptome data by the described Bayesian network model may provide the necessary information on Wnt activity in breast cancer, which will allow for a more reliable prediction of therapy response to drugs targeting the Wnt cellular signaling pathway.

While in the above description, a normal distribution having a mean value μ and a standard deviation σ is used in the estimation of the continuous probability distribution of the observations of the child node for each of the two (or more) states of the parent node, the continuous probability distribution can also be another probability distribution, such as a probability distribution that is estimated using a kernel density estimation (KDE).

The described computer-implemented Bayesian inference method can be realized by a suitable Bayesian inference device, which comprises a suitable providing unit for performing step a) of the method and a suitable inferring unit for performing step b) of the method. In case step a), i.e., the step of providing a continuous probability distribution of the observations of the child node for each of the two states of the parent node based on values of observations of the child node for which the state of the parent node is known includes the actual calibration, i.e., the estimation of the continuous probability distributions based on the values of the observations of the child node for which the state of the parent node is known, the providing unit is adapted to perform such calibration. Alternatively, in case the calibrating has already occurred during an earlier phase (e.g., a research phase) and step a) only includes the providing of the already calibrated Bayesian network for performing step b), i.e., the step of inferring for a new observation of the child node for which the state of the parent node is not known the probability of at least a first state of the two states of the parent node, the providing unit is adapted to provide the already calibrated Bayesian network.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage. Operations like the providing of a continuous probability distribution of the observations of the child node for each of the two (or more) states of the parent node based on values of observations of the child node for which the state of the parent node is known or the inferring for a new observation of the child node for which the state of the parent node is not known of the probability of at least a first state of the two (or more) states of the parent node, performed by one or several units or devices can be performed by any other number of units or devices. These operations can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a computer-implemented Bayesian inference method for performing Bayesian inference in a Bayesian network, which includes a continuous child node and its discrete parent node having two states, wherein the computer-implemented Bayesian inference method comprises:
  a) providing a continuous probability distribution of the observations of the child node for each of the two states of the parent node based on values of observations of the child node for which the state of the parent node is known, and
  b) inferring for a new observation of the child node for which the state of the parent node is not known the probability of at least a first state of the two states of the parent node, wherein the inferring includes calculating (i) for the lower-located probability distribution, which is located at the relatively lower location with respect to the values of the observations of the child node, the mass of the portion of the probability distribution being larger than the value of the new observation of the child node and (ii) for the higher-located probability distribution, which is located at the relatively higher location with respect to the observations of the child node, the mass of the portion of the probability distribution being smaller than the value of the new observation of the child node, and calculating the probability of the first state based on the calculated masses.

The invention claimed is:

1. A computer-implemented Bayesian inference method for performing Bayesian inference in a Bayesian network, which includes a continuous child node and discrete parent node of the child node, the discrete parent node having two states, wherein the computer-implemented Bayesian inference method comprises:
  a) providing continuous probability distributions of observations of the child node fore the two states of the parent node, respectively, based on values of observations of the child node for which the states of the parent node are known, wherein the probability distributions comprise a lower-located probability distribution at a relatively lower location with respect to the values of the observations of the child node and a higher-located probability distribution at a relatively higher location with respect to the values of the observations of the child node; and
  b) inferring for a new observation of the child node, for which the state of the parent node is not known, a probability of at least a first state of the two states of the parent node, wherein the inferring includes calculating (i) for the lower-located probability distribution, a mass of a portion of the lower-located probability distribution that is larger than a value of the new observation of the child node and (ii) for the higher-located probability distribution, a mass of a portion of the richer-located probability distribution that is smaller than the value of the new observation of the child node, and calculating the probability of the first state based on the calculated masses.

2. The computer-implemented Bayesian inference method of in claim 1, wherein the calculating of the masses includes determining which of the probability distributions is the lower-located probability distribution and which is the higher-located probability distribution based on a location parameter of the probability distributions.

3. The computer-implemented Bayesian inference method of claim 2, wherein the location parameter of the probability distributions is a mean value of a median value.

4. The computer-implemented Bayesian inference method of claim 1, wherein the calculating of the probability of the first state includes normalizing one of the calculated masses by the sum of the calculated masses.

5. The computer-implemented Bayesian inference method as of claim 1, wherein the inferring of the probability of the first state further includes transforming the calculated probability of the first state, wherein the transforming depends on a measure of similarity of the probability distributions.

6. The computer-implemented Bayesian inference method of claim 5, wherein the transforming includes scaling the calculated probability of the first state and applying an offset to the scaled calculated probability of the first state.

7. The computer-implemented Bayesian inference method of claim 6, wherein the scaling includes performing a comparison of the probability distributions or of the observations of the child node on which the probability distributions are based to determine the measure of similarity, and scaling the calculated probability of the first state in dependence of a function of the determined measure of similarity.

8. The computer-implemented Bayesian inference method of claim 7, wherein the function of the determined measure of similarity is a linear function.

9. The computer-implemented Bayesian inference method of claim 7, wherein the function of the determined measure of similarity is a non-linear function.

10. The computer-implemented Bayesian inference method of claim 9, wherein the non-linear function comprises a Hill function.

11. The computer-implemented Bayesian inference method of claim 1, wherein the parent node has further states, wherein the continuous probability distribution of the observations of the child node is provided for each of the states of the parent node, wherein the masses are calculated for successive pairs of the states of the parent node and the probability of the first state is calculated based on the calculated masses.

12. The computer-implemented Bayesian inference method of claim 11, wherein the calculating of the probability of the first state includes calculating odds between successive states of the parent node based on the calculated masses for the states.

13. The computer-implemented Bayesian inference method of claim 12, wherein the probability of the first state is calculated based on a product of the calculated odds.

14. A Bayesian inference device for performing Bayesian inference in a Bayesian network, which includes a continuous child node and a discrete parent node of the child node, the discrete parent node having two states, wherein the Bayesian inference device comprises:
   a computer; and
   a non-transitory storage medium storing instructions that, when executed by the computer, cause the computer to:
   provide continuous probability distributions of observations of the child node for the two states of the parent node, respectively, based on values of observations of the child node for which the states of the parent node are known, wherein the probability distributions comprise a lower-located probability distribution at a relatively lower location with respect to the values of the observations of the child node and a higher-located probability distribution at a relatively higher location with respect to the values of the observations of the child node; and
   infer for a new observation of the child node, for which the state of the parent node is not known, a probability of at least a first state of the two states of the parent node, wherein the inferring includes calculating (i) for the lower-located probability distribution, a mass of a portion of the lower-located probability distribution that is larger than a value of the new observation of the child node and (ii) for the higher-located probability distribution, a mass of a portion of the richer-located probability distribution that is smaller than the value of the new observation of the child node, and calculating the probability of the first state based on the calculated masses.

15. The Bayesian inference device of claim 14, wherein the instructions cause the computer to calculate the probability of the first state by normalizing one of the calculated masses by the sum of the calculated masses.

16. The Bayesian inference device of claim 14, wherein the instructions cause the computer to infer of the probability of the first state by further transforming the calculated probability of the first state, wherein the transforming depends on a measure of similarity of the probability distributions, and includes scaling the calculated probability of the first state and applying an offset to the scaled calculated probability of the first state.

17. A method for inferring activity of a cellular signaling pathway using probabilistic modelling of target gene expressions, wherein the method comprises:
   inferring the activity of the cellular signaling pathway in a medical subject based at least on expression levels of one or more target genes of the cellular signaling pathway measured in an extracted sample of the medical subject, wherein the inferring comprises:
   determining an activity level of a transcription factor element in the extracted sample of the medical subject, the transcription factor element controlling transcription of the one or more target genes of the cellular signaling pathway, the determining being based at least in part on evaluating a Bayesian network according to the method of claim 1 relating expression levels of the one or more target genes of the cellular signaling pathway to the activity level of the transcription factor element; and
   inferring the activity of the cellular signaling pathway in the medical subject based on the determined activity level of the transcription factor element in the extracted sample of the medical subject.

18. The method of as defined in claim 17, further comprising:
   determining whether the cellular signaling pathway is operating abnormally in the medical subject based on the inferred activity of the cellular signaling pathway in the medical subject.

19. The method of claim 17, further comprising:
   recommending prescribing a drug for the medical subject that corrects for abnormal operation of the cellular signaling pathway,
   wherein the recommending is performed when the cellular signaling pathway is determined to be operating abnormally in the medical subject based on the inferred activity of the cellular signaling pathway.

20. A non-transitory computer readable medium storing instructions for performing Bayesian inference in a Bayesian network, which includes a continuous child node and a discrete parent node of the child node, the discrete parent node having two states, wherein when executed by a computer, the instructions cause the computer to:
   provide continuous probability distributions of observations of the child node for the two states of the parent node, respectively, based on values of observations of the child node for which the states of the parent node are known, wherein the probability distributions comprise a lower-located probability distribution at a relatively lower location with respect to the values of the observations of the child node and a higher-located probability distribution at a relatively higher location with respect to the values of the observations of the child node; and
   infer for a new observation of the child node, for which the state of the parent node is not known, a probability of at least a first state of the two states of the parent node, wherein the probability of at least the first state is inferred by calculating (i) a mass of a portion of the lower-located probability distribution that is larger than a value of the new observation of the child node and (ii) a mass of a portion of the higher-located probability distribution that is smaller than the value of the new observation of the child node, and calculating the probability of the first state based on the calculated masses.

* * * * *